United States Patent
Kobayashi (10) Patent No.: US 9,280,638 B2
(45) Date of Patent: Mar. 8, 2016

(54) IMAGE PROCESSING APPARATUS AND METHOD, AND NON-TRANSITORY COMPUTER READABLE MEDIUM

(71) Applicant: FUJI XEROX CO., LTD., Minato-ku, Tokyo (JP)

(72) Inventor: Kunihiko Kobayashi, Kanagawa (JP)

(73) Assignee: FUJI XEROX CO., LTD., Minato-ku (JP)

(*) Notice: Subject to any disclaimer, the term of this patent is extended or adjusted under 35 U.S.C. 154(b) by 0 days.

(21) Appl. No.: 14/450,894

(22) Filed: Aug. 4, 2014

(65) Prior Publication Data

US 2015/0205920 A1    Jul. 23, 2015

(30) Foreign Application Priority Data

Jan. 17, 2014  (JP) ................................. 2014-007224

(51) Int. Cl.
  *G06F 19/00*  (2011.01)
  *H04N 1/387*  (2006.01)
  *H04N 1/04*  (2006.01)

(52) U.S. Cl.
  CPC ............ *G06F 19/322* (2013.01); *H04N 1/3873* (2013.01)

(58) Field of Classification Search
  CPC ........... G06F 19/322; H04N 1/04; H04N 1/38
  USPC .................................. 358/450, 780, 474, 468
  See application file for complete search history.

(56) References Cited

U.S. PATENT DOCUMENTS 6,646,765 B1 * 11/2003 Barker et al. ................. 358/474
2008/0195965 A1 * 8/2008 Pomerantz .................... 715/780

FOREIGN PATENT DOCUMENTS

JP        2007-4621 A     1/2007
JP        2010-102734 A   5/2010

* cited by examiner

*Primary Examiner* — Quang N Vo
(74) *Attorney, Agent, or Firm* — Sughrue Mion, PLLC (57) ABSTRACT

An image processing apparatus includes a deleted differential image generator and a region specifying unit. The deleted differential image generator generates, from first image data generated by reading an image of an unfilled or filled-in sheet and second image data generated by reading an image of a sheet being in a format identical to the unfilled or filled-in sheet and having a superimposed sheet superimposed thereon, deleted differential image data representing an image that is not represented in the second image data but is represented in the first image data. The region specifying unit specifies a region where the superimposed sheet is represented in the second image data, based on a region where the deleted differential image data is.

19 Claims, 10 Drawing Sheets

IMAGE PROCESSING APPARATUS AND METHOD, AND NON-TRANSITORY COMPUTER READABLE MEDIUM

CROSS-REFERENCE TO RELATED APPLICATIONS

This application is based on and claims priority under 35 USC 119 from Japanese Patent Application No. 2014-007224 filed Jan. 17, 2014.

BACKGROUND (i) Technical Field

The present invention relates to an image processing apparatus and method, and to a non-transitory computer readable medium.

(ii) Related Art

There is a system that converts a paper document to electronic data, and enables browsing of the data with a personal computer or the like. For example, electronic image data is generated by reading a paper document with a reading apparatus such as a scanner. By converting a paper document to electronic data as described here, a system with superior sharingness, portability, and retrievability is configured, thereby enhancing the convenience of users.

By the way, in the medical field, there are cases in which electronic data such as electronic medical records is used in order to enable sharing of information among distant facilities or related organizations (such as hospitals, clinics, pharmacies, visiting nurse stations, and nursing homes). In contrast, electronic medical records may not be adopted in relatively small hospitals or clinics. In addition, not all items of information are converted to electronic data even among medical institutions where electronic medical records are adopted, and meaningful information necessary for medical consultation may sometimes be exchanged in the form of paper documents. Further, there are needs for using paper records as they are. As described here, in the case where a paper document is used, sharing of information involves transmission of the paper document to a destination via facsimile or in the form of a duplicate copy, which is bothersome. Thus, the original paper document (such as a medical record) may be converted to electronic image data, and the electronic image data may be stored in a common server or the like, thereby enabling sharing of the information. Note that items of information other than medical records (such as test information, nursing records, care notes, and prescription information) may also be converted to electronic data, and the data may be stored in a common server or the like, thereby enabling sharing of the information.

In addition, a patient's consultation record is written on a medical record, and a test slip for a test such as a blood test, a urinalysis, or a biomedical test may be appended to the medical record. This is done to prevent the test slip from being lost or mixed into another place, and to enable the test slip to be browsed in accordance with chronological records on the medical record. For example, in the case where test slips are attached to a certain patient's paper records, if a person wants to compare a test result at a certain consultation time with a past test result, it is necessary for this person to find a past paper medical record and to browse the medical record for a comparison, which is bothersome.

In the case where paper medical records are converted to electronic image data, it is conceivable to alternately display multiple medical records to be compared on a display and to enable browsing of these medical records. In this case, it is necessary to alternately switch the images, which is similarly bothersome as with the case of paper medical records. In addition, it is conceivable to divide the screen of a display, arrange the images of a patient's multiple medical records in units of pages, and enable browsing of the images. In this case, it is necessary to secure the size of divided screens in order to enable the images of medical records to be displayed in units of pages. This restricts the number of divided screens and the number of medical records displayed side by side. As described here, the number of divided screens is restricted depending on the size of medical records. Even if a test slip attached to a medical record is relatively small, the number of test slips displayed side by side is restricted, thereby reducing the convenience in browsing the test results for a comparison. For example, since the images of medical records are displayed in units of pages, if the number of divided screens is restricted to two, only the images of two medical records are displayed side by side on the display. In this case, a test slip attached to each medical record is displayed on the display. Since only the two medical records are displayed, the number of test slips displayed side by side is also restricted to two. As described here, even though test slips are smaller than medical records, the number of test slips displayed side by side is restricted, thereby reducing the convenience in browsing the test results for a comparison. This is not limited to test slips; a similar problem occurs in the case of other notes or the like attached to medical records.

SUMMARY

According to an aspect of the invention, there is provided an image processing apparatus including a deleted differential image generator and a region specifying unit. The deleted differential image generator generates, from first image data generated by reading an image of an unfilled or filled-in sheet and second image data generated by reading an image of a sheet being in a format identical to the unfilled or filled-in sheet and having a superimposed sheet superimposed thereon, deleted differential image data representing an image that is not represented in the second image data but is represented in the first image data. The region specifying unit specifies a region where the superimposed sheet is represented in the second image data, based on a region where the deleted differential image data is.

BRIEF DESCRIPTION OF THE DRAWINGS

An exemplary embodiment of the present invention will be described in detail based on the following figures, wherein.

DETAILED DESCRIPTION

Figure 1:
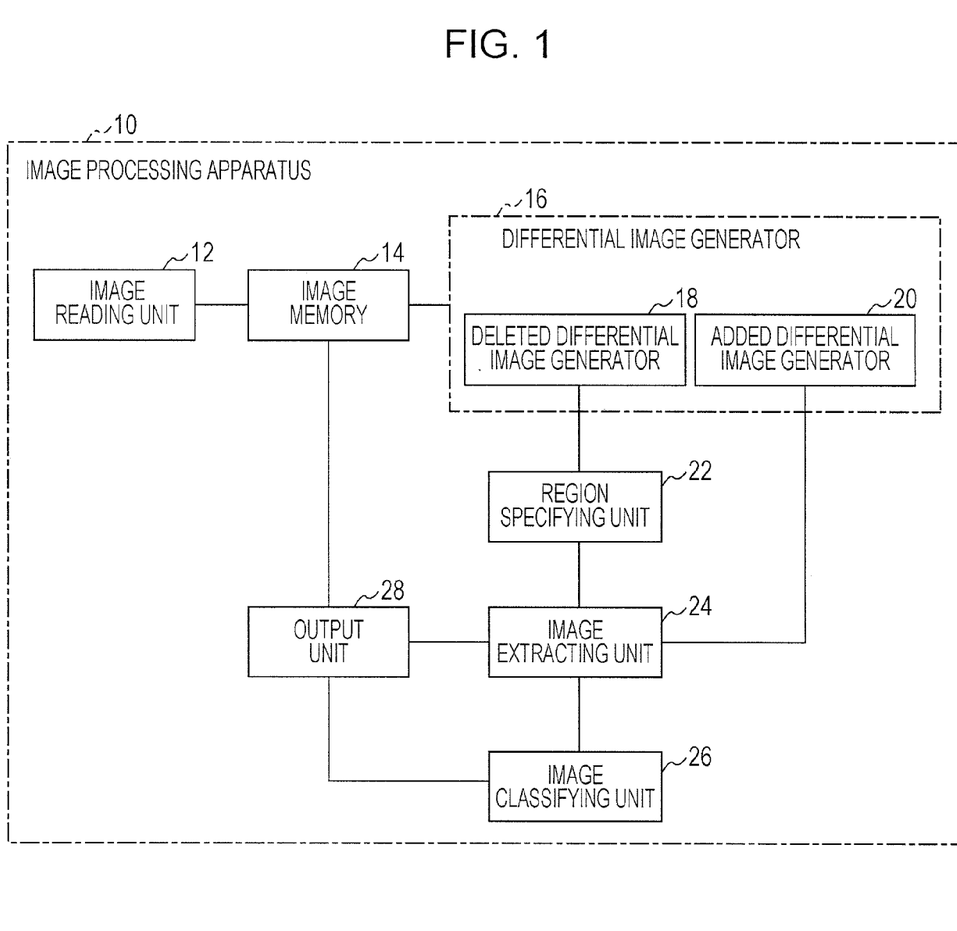
FIG. 1 is a block diagram illustrating an example of an image processing apparatus according to an exemplary embodiment of the invention.

FIG. 1 illustrates an exemplary image processing apparatus according to an exemplary embodiment of the invention. An image processing apparatus 10 according to the exemplary embodiment includes an image reading unit 12, an image memory 14, a differential image generator 16, a region specifying unit 22, an image extracting unit 24, an image classifying unit 26, and an output unit 28. The differential image generator 16 includes a deleted differential image generator 18 and an added differential image generator 20. Note that the image processing apparatus 10 may have the function of being connected to an external apparatus such as a server (not illustrated) or a terminal apparatus (not illustrated) via a communication channel such as a network, transmitting various types of data such as image data, and receiving data from the external apparatus.

Figure 2A:
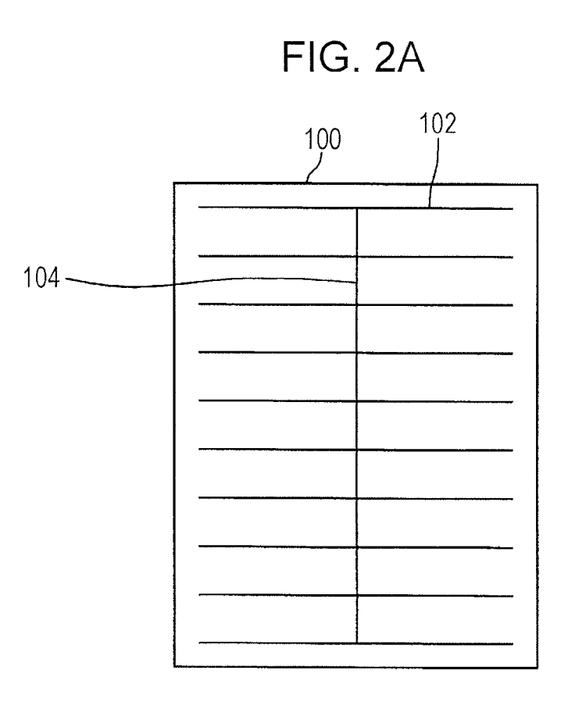
FIG. 2A is a schematic diagram illustrating an exemplary medical record.
Figure 2B:
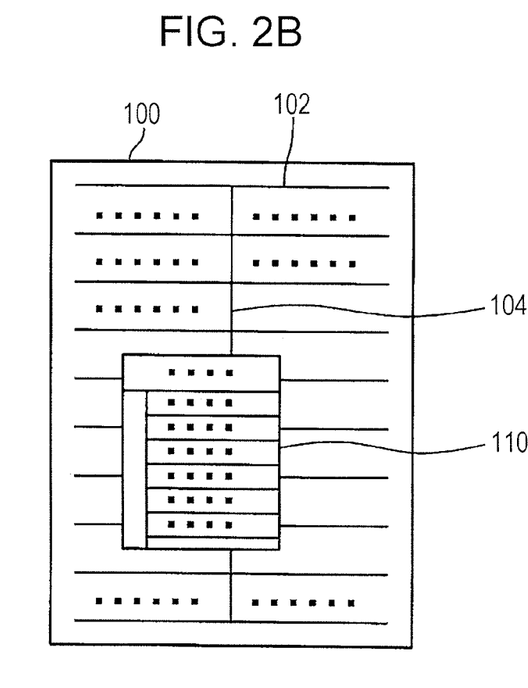
FIG. 2B is a schematic diagram illustrating an exemplary superimposed sheet.

First, with reference to FIGS. 2A and 2B, an exemplary sheet handled in the exemplary embodiment will be described. FIGS. 2A and 2B schematically illustrate an exemplary paper medical record used in a medical institution such as a hospital.

FIG. 2A illustrates a paper medical record 100 that has not been filled in yet. The medical record 100 is generated in accordance with a predetermined format, and lines 102 and 104 are drawn in advance on the medical record 100 by printing or the like. For example, the lines 102 extend in the horizontal direction (first direction) of the medical record 100 and are drawn at an interval along the vertical direction (second direction) of the medical record 100. In addition, the line 104 is drawn intersecting the lines 102 and extending in the vertical direction (second direction). The medical record 100 corresponds to, for example, a Japanese medical record No. 2 sheet; however, a medical record in another format may be used. For example, multiple lines 104 may be drawn at an interval along the horizontal direction.

FIG. 2B illustrates the paper medical record 100, which has been filled in. For example, a doctor writes a character string ("..." in FIG. 2B), a figure, a table, or the like on the medical record 100, or a doctor, a medical technologist, or a nurse attaches a superimposed sheet 110 on the medical record 100. The superimposed sheet 110 is smaller than the medical record 100 and is attached to the medical record 100 by glue, for example. The shape of the superimposed sheet 110 is rectangular, for example. The superimposed sheet 110 is, for example, a test slip, a nursing record, a care note, or a prescription slip. The test slip includes the result of various tests, such as a blood test, a urinalysis, or a biomedical test. When the superimposed sheet 110 is attached to the medical record 100 as described here, a portion of the medical record 100 where the superimposed sheet 110 is attached is covered with the superimposed sheet 110. In the example illustrated in FIG. 2B, the lines 102 and 104 below the superimposed sheet 110 are covered with the superimposed sheet 110.

Referring back to FIG. 1, the image reading unit 12 is an image reading apparatus such as a scanner or a digital camera, and generates electronic image data by reading an image on a sheet. The image memory 14 stores image data generated by the image reading unit 12.

In the exemplary embodiment, the image reading unit 12 generates image data (hereinafter referred to as "medical record format image data") representing the unfilled medical record 100, which is illustrated in FIG. 2A, by reading an image of the unfilled medical record 100. In addition, the image reading unit 12 generates image data (hereinafter referred to as "medical record image data") representing the filled-in medical record 100 by reading an image of the filled-in medical record 100. The image reading unit 12 generates medical record image data by reading an image of the medical record 100 to which the superimposed sheet 110 is attached, as illustrated in FIG. 2B, for example.

Note that medical record image data generated by the image reading unit 12 is supplemented by, for example, a controller (not illustrated) with patient identification information such as the name and ID of the patient, and information indicating the occurrence date of an event such as a medical consultation. For example, a folder is generated for each patient and for each event in the image memory 14, and medical record image data is stored in each folder. In addition, medical record image data may be transmitted to an external apparatus such as a server from the image processing apparatus 10 via a communication channel such as a network and may be stored in the external apparatus. Medical record image data may be put in a state in which the medical record image data is browsable by users with various occupations. For example, medical record image data may be browsed by a doctor, a nurse, or a pharmacist in accordance with his/her authority.

The deleted differential image generator 18 detects a difference between medical record format image data representing the unfilled medical record 100 and medical record image data representing the filled-in medical record 100, and generates deleted differential image data representing an image that is represented in the medical record format image data but is not represented in the medical record image data. That is, the deleted differential image generator 18 compares medical record format image data with medical record image data, and extracts image data of a portion of the medical record image data, which has been deleted from the medical record format image data (deleted differential image data). In the exemplary embodiment, the deleted differential image generator 18 generates deleted differential image data representing a portion (lines 102 and 104) covered with the superimposed sheet 110.

The added differential image generator 20 detects a difference between medical record format image data representing the unfilled medical record 100 and medical record image data representing the filled-in medical record 100, and generates added differential image data representing an image that is not represented in the medical record format image data but is represented in the medical record image data. That is, the added differential image generator 20 extracts image data of a portion added to the medical record format image data (added differential image data).

The region specifying unit 22 specifies a region of the superimposed sheet 110 attached to the filled-in medical record 100, on the basis of the deleted differential image data generated by the deleted differential image generator 18. That is, the region specifying unit 22 specifies a region of the superimposed sheet 110 represented in the medical record image data or the added differential image data.

Figure 3A:
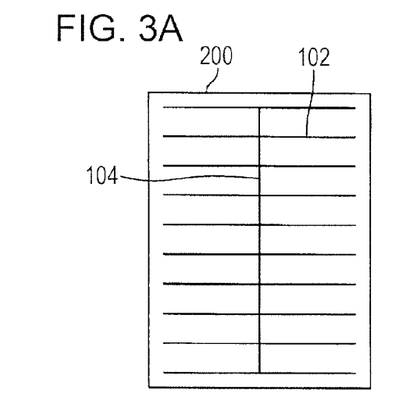
FIGS. 3A to 3E are schematic diagrams illustrating exemplary images.
Figure 3B:
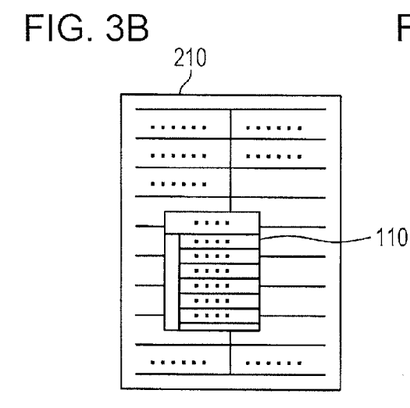

Here, with specific examples illustrated in FIGS. 3A to 3E, a process performed by the deleted differential image generator 18, the added differential image generator 20, and the region specifying unit 22 will be described. FIG. 3A illustrates an example of medical record format image data 200 generated by the image reading unit 12, and FIG. 3B illustrates an example of medical record image data 210 generated by the image reading unit 12.

Figure 3C:
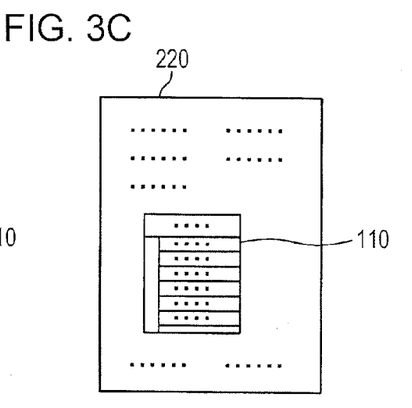

The added differential image generator 20 detects a difference between the medical record format image data 200 and the medical record image data 210, and, as illustrated in FIG. 3C, generates added differential image data 220 representing a portion added to the medical record format image data 200. Since the added differential image data 220 is image data representing a portion added to the medical record format image data 200, the lines 102 and 104 represented in the medical record format image data 200 are not represented in the added differential image data 220, and a character string written on the medical record 100 and the superimposed sheet 110 are represented in the added differential image data 220.

Figure 3D:
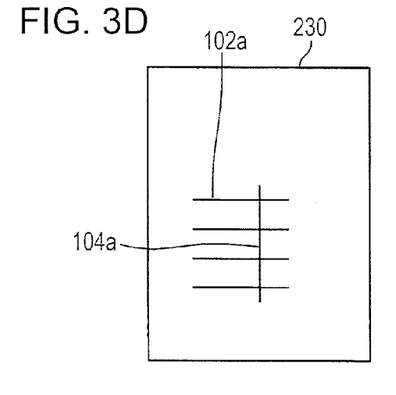

The deleted differential image generator 18 detects a difference between the medical record format image data 200 and the medical record image data 210, and, as illustrated in FIG. 3D, generates deleted differential image data 230 representing a portion deleted in the medical record image data 210 from the medical record format image data 200. For example, as illustrated in FIG. 2B, when the superimposed sheet 110 is attached to the medical record 100, the lines 102 and 104 below the superimposed sheet 110 are covered. Thus, as illustrated in FIG. 3B, the lines 102 and 104 covered with the superimposed sheet 110 are not represented in the medical record image data 210. The deleted differential image generator 18 detects a difference between the medical record format image data 200 and the medical record image data 210, and detects an image that is represented in the medical record format image data 200 but is not represented in the medical record image data 210, thereby generating the deleted differential image data 230 of a portion covered with the superimposed sheet 110, where lines 102a and 104a are represented, as illustrated in FIG. 3D.

Figure 3E:
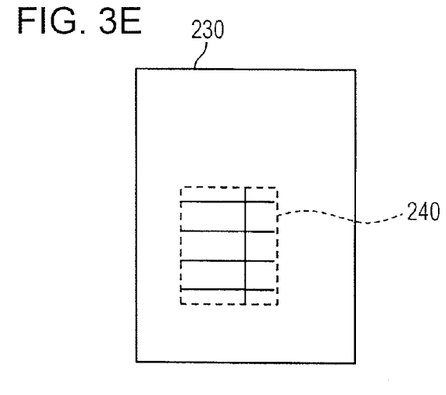

Using the lines represented in the deleted differential image data 230, the region specifying unit 22 specifies the position of a region where the superimposed sheet 110 is represented in the medical record image data 210 (hereinafter referred to as a "superimposed sheet region"). That is, the region specifying unit 22 specifies a position where the superimposed sheet 110 is attached on the medical record 100. For example, with reference to the ends of the lines 102a and 104a represented in the deleted differential image data 230, the region specifying unit 22 specifies the contour of the superimposed sheet region. For example, the region specifying unit 22 detects the positions of the right and left ends of each line 102a extending in the horizontal direction of the deleted differential image data 230, and detects the positions of the top and bottom ends of the line 104a extending in the vertical direction. The region specifying unit 22 defines a line segment that passes the left end of each line 102a and that is parallel to the line 104 (or line 104a) as the left side of the superimposed sheet region, and defines a line segment that passes the right end of each line 102a and that is parallel to the line 104 (or line 104a) as the right side of the superimposed sheet region. In addition, the region specifying unit 22 defines a line segment that passes the top end of the line 104a and that is parallel to the lines 102 (or lines 102a) as the top side of the superimposed sheet region, and defines a line segment that passes the bottom end of the line 104a and that is parallel to the lines 102 (or lines 102a) as the bottom side of the superimposed sheet region. The region specifying unit 22 defines the left side, right side, top side, and bottom side as the boundary of the superimposed sheet region, and a region surrounded by the left side, right side, top side, and bottom side as the superimposed sheet region. FIG. 3E illustrates an example of a superimposed sheet region 240 specified by the region specifying unit 22. Since the shape of the superimposed sheet 110 is rectangular, for example, the shape of the superimposed sheet region 240 is rectangular.

Figure 4:
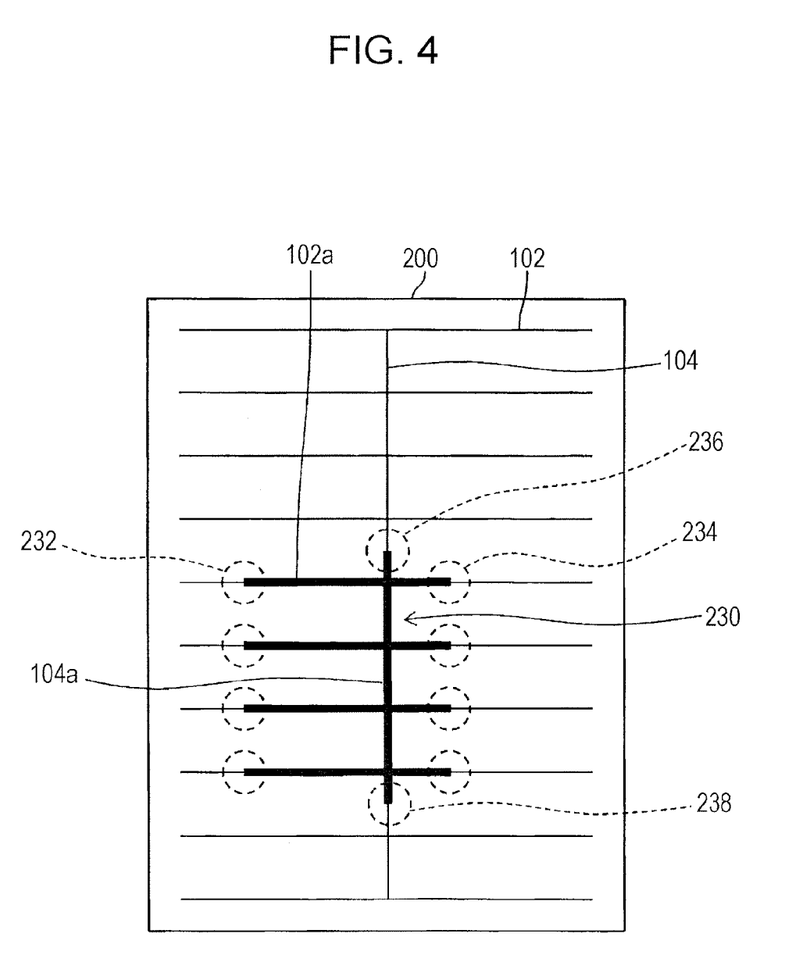
FIG. 4 is a schematic diagram illustrating an exemplary image.

Here, with reference to FIG. 4, another example for specifying the superimposed sheet region 240 will be described. First, the region specifying unit 22 superimposes the lines 102a and 104a (bold lines in FIG. 4), represented in the deleted differential image data 230, on the lines 102 and 104, represented in the medical record format image data 200, as illustrated in FIG. 4. The region specifying unit 22 compares the positions of the lines 102 and 104 represented in the medical record format image data 200 with the positions of the lines 102a and 104a represented in the deleted differential image data 230, and specifies positions adjacent to the ends of the lines 102a and 104a as the positions of sides (boundary) of the superimposed sheet region 240. For example, in the lines 102 represented in the medical record format image data 200, the region specifying unit 22 specifies positions adjacent to left ends 232 of the horizontal lines 102a represented in the deleted differential image data 230 as the position of the left side of the superimposed sheet region 240. In the example illustrated in FIG. 4, the positions of the left ends 232 of the lines 102a correspond to the position of the left side of the superimposed sheet region 240. In addition, in the lines 102 represented in the medical record format image data 200, the region specifying unit 22 specifies positions adjacent to right ends 234 of the horizontal lines 102a represented in the deleted differential image data 230 as the position of the right side of the superimposed sheet region 240. In the example illustrated in FIG. 4, the positions of the right ends 234 of the lines 102a correspond to the position of the right side of the superimposed sheet region 240. In addition, in the line 104 represented in the medical record format image data 200, the region specifying unit 22 specifies a position adjacent to a top end 236 of the vertical line 104a represented in the deleted differential image data 230 as the position of the top side of the superimposed sheet region 240. In the example illustrated in FIG. 4, the position of the top end 236 of the line 104a corresponds to the position of the top side of the superimposed sheet region 240. In addition, in the line 104 represented in the medical record format image data 200, the region specifying unit 22 specifies a position adjacent to a bottom end 238 of the vertical line 104a represented in the deleted differential image data 230 as the position of the bottom side of the superimposed sheet region 240. In the example illustrated in FIG. 4, the position of the bottom end 238 of the line 104a corresponds to the position of the bottom side of the superimposed sheet region 240. The region specifying unit 22 specifies a region surrounded by the left side, right side, top side, and bottom side as the superimposed sheet region 240. By specifying the superimposed sheet region 240 as described here, whether the ends of the lines 102a and 104a represented in the deleted differential image data 230 correspond to the ends of the lines 102 and 104 of the medical record 100 or to positions somewhere in the middle of the lines 102 and 104 is specified. Note that the example for specifying the superimposed sheet region 240 is not limited to the above-described example. For example, a rectangular region circumscribed about the deleted differential image data 230 illustrated in FIG. 3D may be obtained, and that rectangular region may be specified as the superimposed sheet region 240.

Figure 5A:
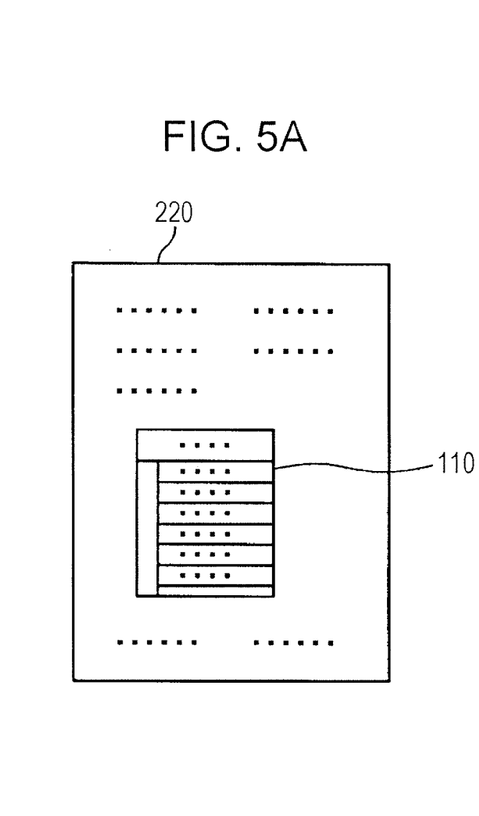
FIGS. 5A to 5C are schematic diagrams illustrating exemplary images.
Figure 5B:
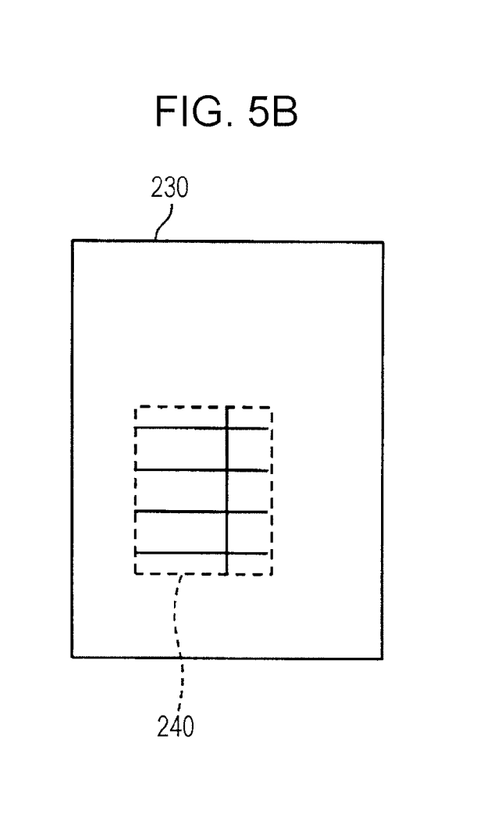
Figure 5C:
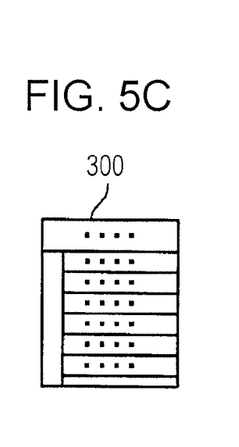

The image extracting unit 24 specifies the position of the superimposed sheet region 240 in the medical record image data 210 or the added differential image data 220 on the basis of the position of the superimposed sheet region 240 specified by the region specifying unit 22, and extracts image data in the superimposed sheet region 240 from the medical record image data 210 or the added differential image data 220. For example, the image extracting unit 24 extracts image data in the superimposed sheet region 240 illustrated in FIG. 5B from the added differential image data 220 illustrated in FIG. 5A. Accordingly, as illustrated in FIG. 5C, superimposed sheet image data 300 where the superimposed sheet 110 is represented is generated. Note that the image extracting unit 24 may supplement the superimposed sheet image data 300 with supplementary information (such as patient information and information on an event) added as a supplement to the medical record image data 210.

Figure 6:
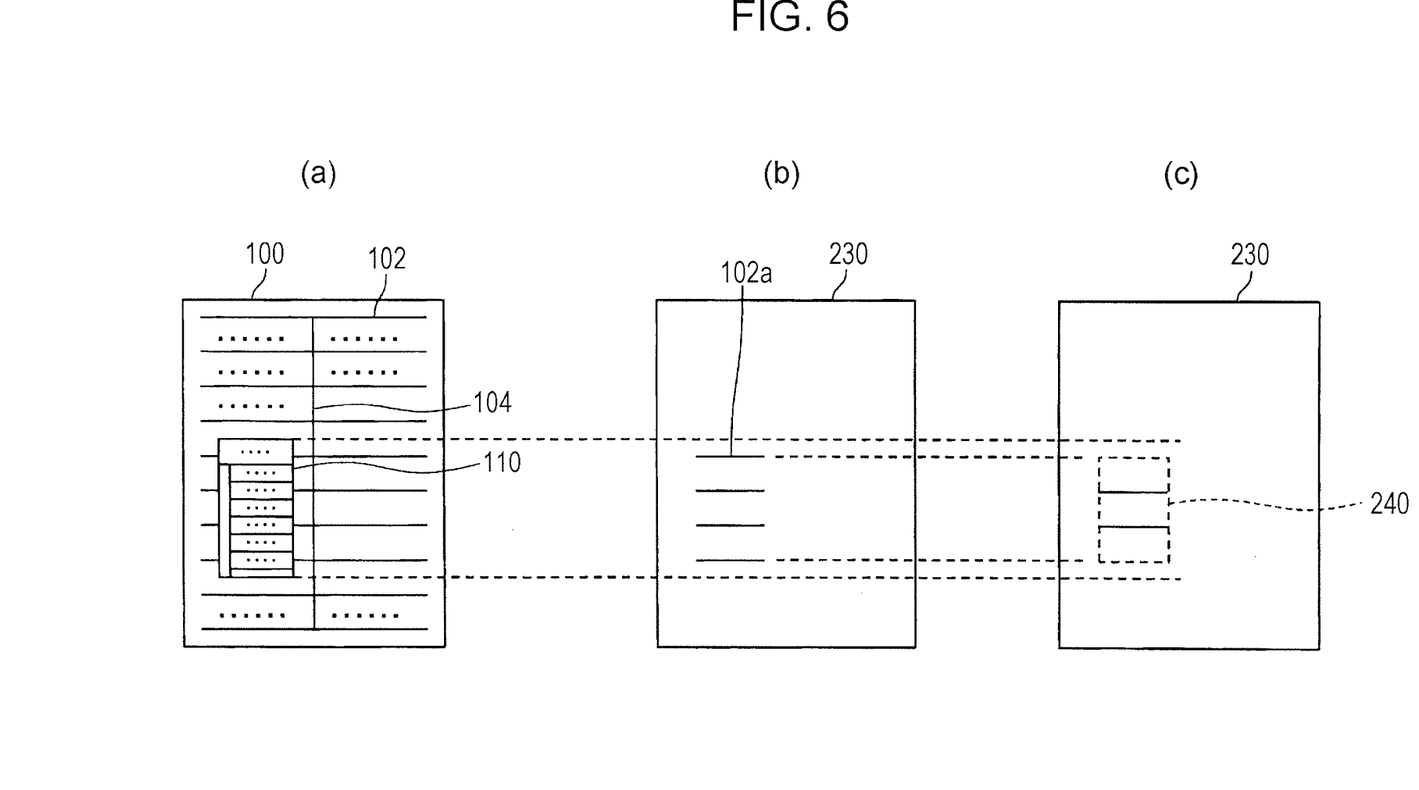
FIG. 6 is a schematic diagram illustrating an exemplary medical record and exemplary images.
Figure 7:
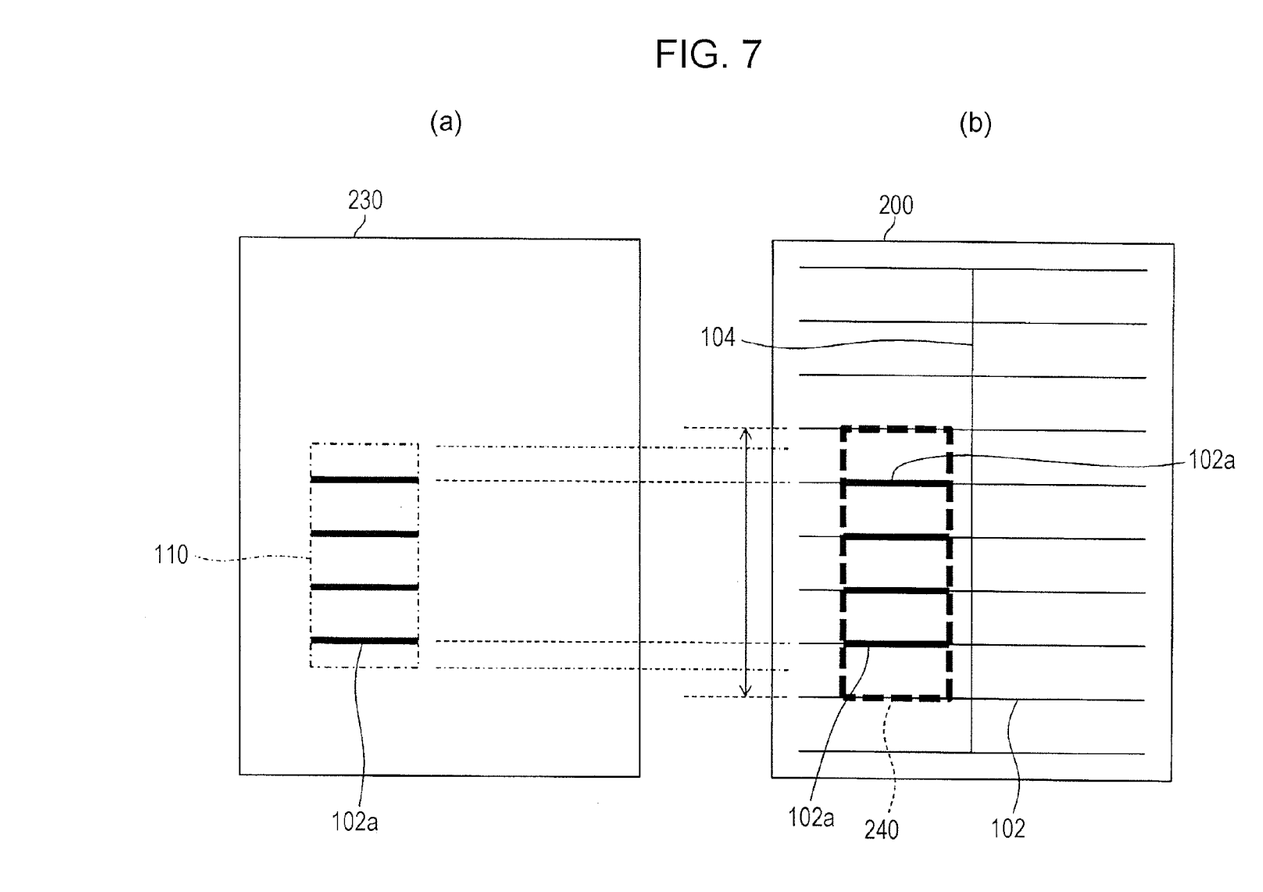
FIG. 7 is a schematic diagram illustrating exemplary images.

Here, referring to FIGS. 6 and 7, another example of the deleted differential image data 230 will be described. For example, as illustrated in part (a) of FIG. 6, the line 104 extending in the vertical direction may not be covered with the superimposed sheet 110, depending on a position at which the superimposed sheet 110 is attached to the medical record 100. In this case, for example, as illustrated in part (b) of FIG. 6, only the lines 102a in a portion covered with the superimposed sheet 110 are represented in the deleted differential image data 230, and the line 104 is not represented. In the case where the line 104 extending in the vertical direction is not represented in the deleted differential image data 230 as described here, as illustrated in part (c) of FIG. 6, the line 102a at the top among the lines 102a is defined as the top side of the superimposed sheet region 240, and the line 102a at the bottom among the lines 102a is defined as the bottom side of the superimposed sheet region 240. In doing so, the superimposed sheet region 240 may become narrower than the superimposed sheet 110 that has been actually attached to the medical record 100. For example, as illustrated in part (a) of FIG. 6, if the superimposed sheet 110 is attached to the medical record 100 across the lines 102, the superimposed sheet region 240 becomes narrower than the superimposed sheet 110. If the superimposed sheet image data 300 is extracted using the superimposed sheet region 240 obtained as described here, the entire superimposed sheet 110 is not represented in that superimposed sheet image data 300.

Consequently in the exemplary embodiment, the region specifying unit 22 defines the superimposed sheet region 240 whose size is large enough to contain the entire superimposed sheet 110, by using the lines 102a represented in the deleted differential image data 230 and the lines 102 represented in the medical record format image data 200. This process will be described with reference to FIG. 7. For example, as illustrated in part (a) of FIG. 7, it is assumed that the lines 102a extending in the horizontal direction are represented, but the line 104a extending in the vertical direction is not represented in the deleted differential image data 230. Note that the superimposed sheet 110 is indicated by a dot-and-dash line. In this case, the region specifying unit 22 superimposes the lines 102a, represented in the deleted differential image data 230, on the lines 102 and 104, represented in the medical record format image data 200, as illustrated in part (b) of FIG. 7. The region specifying unit 22 defines the position of the line 102 one above the line 102a at the top among the lines 102a as the top side of the superimposed sheet region 240, and defines the position of the line 102 one below the line 102a at the bottom among the lines 102a as the bottom side of the superimposed sheet region 240. Accordingly, this superimposed sheet region 240 extended in the vertical direction (broken line in part (b) of FIG. 7) is defined. This superimposed sheet region 240 is vertically wider than the superimposed sheet 110 actually attached to the medical record 100, and the entire superimposed sheet 110 is represented in the superimposed sheet image data 300 extracted using this superimposed sheet region 240. In addition, since the expanded range is the interval of two lines 102 including the top and bottom lines 102, the superimposed sheet region 240 is prevented from being unnecessarily expanded. Therefore, even in the case where the expanded superimposed sheet region 240 is used, the superimposed sheet image data 300 from which the surroundings of the superimposed sheet 110 are excluded is extracted. Note that it is sufficient for the left and right sides of the superimposed sheet region 240 to be specified using the method described with reference to FIG. 3E or FIG. 4.

Alternatively, the region specifying unit 22 may define a position separated in the upper direction from the line 102a at the top among the lines 102a represented in the deleted differential image data 230, by a length corresponding to the interval between the lines 102, as the top side of the superimposed sheet region 240, instead of superimposing the deleted differential image data 230 on the medical record format image data 200. Similarly, the region specifying unit 22 may define a position separated in the lower direction from the line 102a at the bottom among the lines 102a represented in the deleted differential image data 230, by a length corresponding to the interval between the lines 102, as the bottom side of the superimposed sheet region 240.

Referring back to FIG. 1, the image classifying unit 26 classifies the superimposed sheet image data 300, extracted by the image extracting unit 24, in accordance with a preset criterion. For example, a test slip, a nursing record, a care note, and a prescription slip have different sizes, colors, shapes, and features. Thus, the image classifying unit 26 specifies the type of the superimposed sheet 110 on the basis of the size, color, shape, and feature of the superimposed sheet 110 represented in the superimposed sheet image data 300, and classifies the superimposed sheet image data 300 into an image group of the same type. In addition, the image classifying unit 26 may obtain the degree of similarity between multiple items of superimposed sheet image data 300, and classify superimposed sheet image data 300 whose degree of similarity is greater than or equal to a preset threshold into the same type. In addition, the image classifying unit 26 may classify the superimposed sheet image data 300 on the basis of supplementary information attached to the superimposed sheet image data 300. For example, the image classifying unit 26 may classify superimposed sheet image data 300 supplemented with the same patient information into the same type, or classify superimposed sheet image data 300 with the same event occurrence date into the same type.

The output unit 28 outputs image data. For example, the output unit 28 has a display, and displays an image. For example, the output unit 28 displays the superimposed sheet image data 300. In addition, the output unit 28 may display the medical record image data 210, or may superimpose the deleted differential image data 230 on the medical record image data 210 and display the result. By superimposing the deleted differential image data 230 on the medical record image data 210, the filled-in medical record 100 to which the superimposed sheet 110 has not been attached is obtained. Note that the output unit 28 may transmit image data to an external apparatus via a communication channel such as a network.

Figure 8:
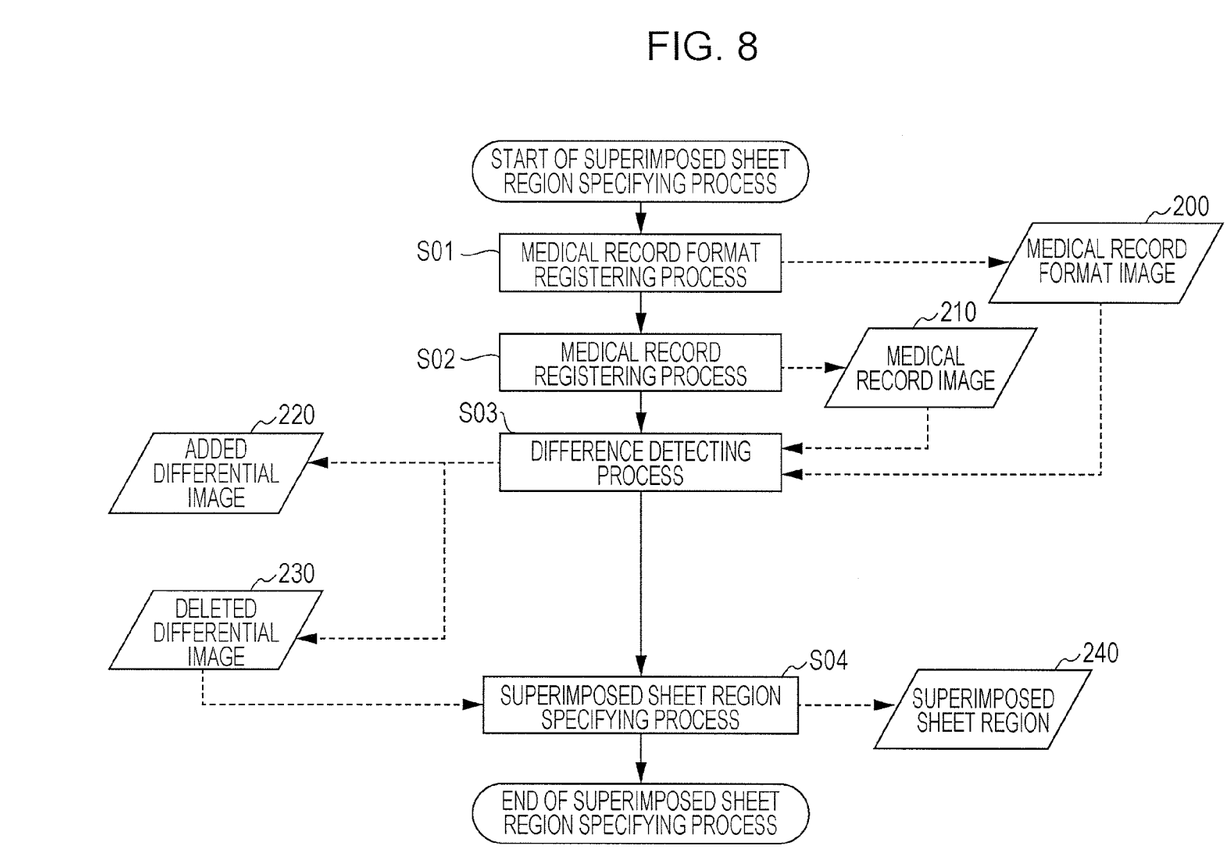
FIG. 8 is a flowchart illustrating an exemplary operation of the image processing apparatus according to the exemplary embodiment.

Next, with reference to the flowchart illustrated in FIG. 8, a process for specifying the superimposed sheet region 240 will be described. First, the format of the unfilled medical record 100 is registered (S01). Specifically, the image reading unit 12 reads an image of the unfilled medical record 100 illustrated in FIG. 2A, thereby generating the medical record format image data 200 illustrated in FIG. 3A. The medical record format image data 200 is stored in the image memory 14. Note that, in the case of using medical records 100 in the same format, it is only necessary to register the medical record format image data 200 once; it is unnecessary to register the medical record format image data 200 every time a differential process is performed.

Next, the filled-in medical record 100 is registered (S02). Specifically, the image reading unit 12 reads an image of the filled-in medical record 100 illustrated in FIG. 2B, thereby generating the medical record image data 210 illustrated in FIG. 3B. Since the superimposed sheet 110 is attached to the filled-in medical record 100, the superimposed sheet 110 is represented in the medical record image data 210.

The differential image generator 16 detects a difference between the medical record format image data 200 and the medical record image data 210 (S03). Specifically, the deleted differential image generator 18 detects a difference between the medical record format image data 200 and the medical record image data 210, and, as illustrated in FIG. 3D, generates the deleted differential image data 230 in which the lines 102a and 104a in a portion covered with the superimposed sheet 110 are represented. In addition, the added differential image generator 20 detects a difference between the medical record format image data 200 and the medical record image data 210, and, as illustrated in FIG. 3C, generates the added differential image data 220 representing a portion added to the medical record format image data 200.

Using the lines 102a and 104a represented in the deleted differential image data 230, as illustrated in FIGS. 3D and 3E, the region specifying unit 22 specifies the position of a region (superimposed sheet region 240) in which the superimposed sheet 110 is represented in the medical record image data 210 (S04).

Figure 9:
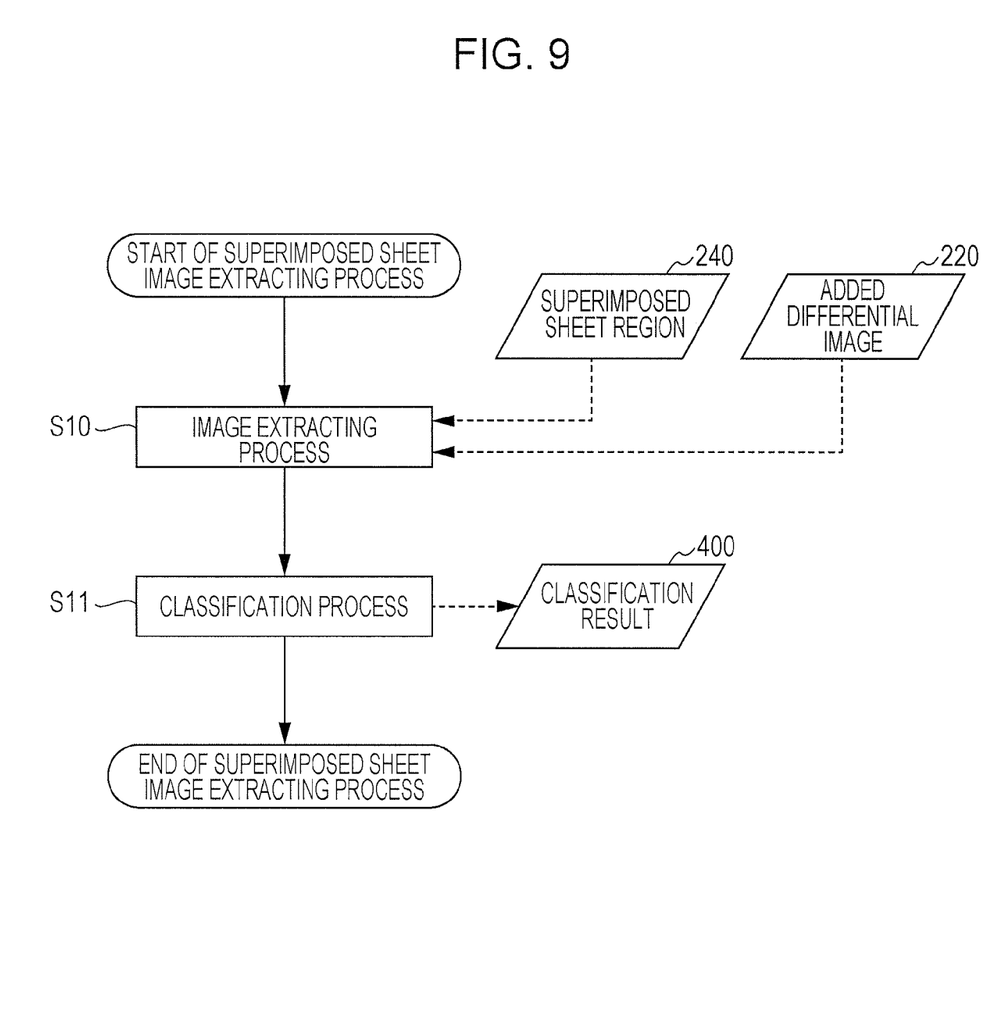
FIG. 9 is a flowchart illustrating an exemplary operation of the image processing apparatus according to the exemplary embodiment.

Next, with reference to the flowchart illustrated in FIG. 9, a process for extracting the superimposed sheet image data 300 will be described. First, the image extracting unit 24 extracts image data in the superimposed sheet region 240 illustrated in FIG. 5B from the added differential image data 220 illustrated in FIG. 5A, thereby generating the superimposed sheet image data 300 illustrated in FIG. 5C (S10). The image classifying unit 26 classifies the superimposed sheet image data 300 on the basis of the size, color, shape, and feature of the superimposed sheet 110 represented in the superimposed sheet image data 300 (S11). Accordingly, a classification result 400 is obtained.

As described above, by using the lines 102 and 104 covered with the superimposed sheet 110, the region of the superimposed sheet 110 (superimposed sheet region 240) represented in the medical record image data 210 is specifiable. The superimposed sheet image data 300 extracted using this superimposed sheet region 240 is image data separated from the medical record image data 210, and the surrounding regions of the superimposed sheet 110 are not represented. Thus, compared with the medical record image data 210 representing the entire medical record 100, the superimposed sheet image data 300 is more suitable for browsing the superimposed sheet 110. For example, since the superimposed sheet 110 is smaller than the medical record 100, the superimposed sheet image data 300 occupies a smaller display region of the display than the medical record image data 210. Thus, it is possible to display side by side a greater number of items of superimposed sheet image data 300 than the medical record image data 210, and hence it becomes easier to browse multiple superimposed sheets 110 for a comparison by using the superimposed sheet image data 300 than using the medical record image data 210. In addition, since the superimposed sheet image data 300 is separable from the medical record image data 210, it becomes easier to classify the superimposed sheet 100, compared with the case in which the medical record image data 210 representing the entire medical record 100 is used.

Figure 10:
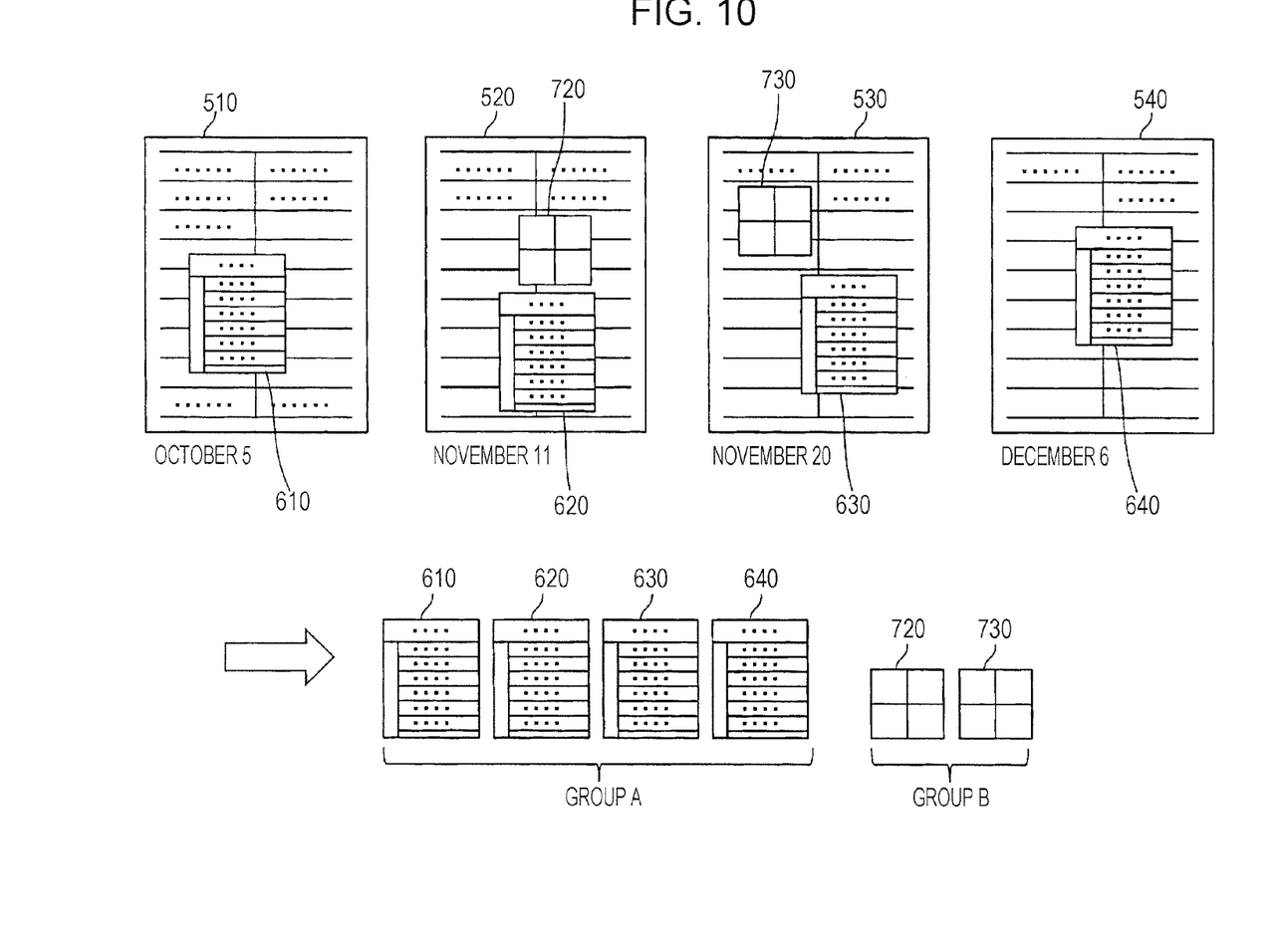
FIG. 10 is a diagram for describing an exemplary application of a process according to the exemplary embodiment.

Next, with reference to FIG. 10, an exemplary application of the exemplary embodiment will be described. Items of medical record image data 510 to 540 illustrated in FIG. 10 are items of image data representing the medical record 100 that have been filled in on different dates. For example, the medical record image data 510 is image data representing the medical record 100 that has been filled in on October 5. The medical record 100 of October 5 has a test slip 610 attached thereto, and the test slip 610 is represented in the medical record image data 510. The medical record image data 520 is image data representing the medical record 100 that has been filled in on November 11. The medical record 100 of November 11 has a test slip 620 and a nursing record 720 attached thereto, and the test slip 620 and the nursing record 720 are represented in the medical record image data 520. The medical record image data 530 is image data representing the medical record 100 that has been filled in on November 20. The medical record 100 of November 20 has a test slip 630 and a nursing record 730 attached thereto, and the test slip 630 and the nursing record 730 are represented in the medical record image data 530. The medical record image data 540 is image data representing the medical record 100 that has been filled in on December 6. The medical record 100 of December 6 has a test slip 640 attached thereto, and the test slip 640 is represented in the medical record image data 540. As described here, the medical record 100 of each date has at least one of a test slip and a nursing record attached thereto as a superimposed sheet.

By applying a process according to the exemplary embodiment to a group of the above-described items of medical record image data 510 to 540, items of superimposed sheet image data 300 representing a superimposed sheet (at least one of a test slip and a nursing record) are extracted from the items of medical record image data 510 to 540, respectively. For example, test slip image data (one example of superimposed sheet image data) representing the test slip 610 is extracted from the medical record image data 510. In addition, test slip image data representing the test slip 620 and nursing record image data (one example of superimposed sheet image data) representing the nursing record 720 are extracted from the medical record image data 520. In addition, test slip image data representing the test slip 630 and nursing record image data representing the nursing record 730 are extracted from the medical record image data 530. In addition, test slip image data representing the test slip 640 is extracted from the medical record image data 540.

On the basis of the size, color, shape, and feature of each of the items of superimposed sheet image data 300, the image classifying unit 26 classifies the superimposed sheet image data 300. For example, because the items of test slip image data representing the test slips 610 to 640 are items of image data representing test slips, these items of test slip image data are regarded as the same type and classified into group A. Because the items of nursing record image data representing the nursing records 720 and 730 are items of image data representing nursing records, these items of nursing record image data are regarded as the same type and classified into group B.

For example, the output unit 28 displays image data classified into the same group. In the example illustrated in FIG. 10, the output unit 28 displays the items of test slip image data representing the test slips 610 to 640, which are classified into group A, side by side, and displays the items of nursing record image data representing the nursing records 720 and 730, which are classified into group B, side by side. Accordingly, it becomes possible to browse multiple test slips (test slips 610 to 640) for a comparison. Similarly, it becomes possible to browse multiple nursing records (nursing records 720 and 730) for a comparison.

Since the test slips 610 to 640 are smaller than the medical record 100, more items of test slip image data are displayed side by side, compared with the case of displaying the items of medical record image data 510 to 540 side by side, and it thus becomes easier to browse the test slips 610 to 640 for a comparison. The same applies to the nursing records 720 and 730. In addition, since the test slips 610 to 640 and the nursing records 720 and 730 are separated from the medical record image data 510 to 540, it becomes easier to classify images of the same type. That is, it becomes easier to classify items of test slip image data representing the test slips 610 to 640 and items of nursing record image data representing the nursing records 720 and 730, thereby facilitating a comparison of superimposed sheets of the same type.

The description so far discusses obtaining a differential image with the medical record image data of a medical record on the basis of medical record format image data corresponding to an unfilled medical record, and specifying a superimposed sheet region. If lines on a medical record that are deleted by attaching a superimposed sheet are extractable as a differential image, it is possible to use other image data, besides an unfilled medical record (medical record format image data), as a criterion for obtaining a differential image from the medical record image data of a medical record to which a superimposed sheet is attached. As this other data, for example, medical record image data before being attached with a superimposed sheet is usable. That is, a differential image between medical record image data before being attached with a superimposed sheet and medical record image data to which a superimposed sheet is attached is obtained, and a superimposed sheet region is specifiable on the basis of the differential image.

The above-described image processing apparatus 10 is realizable by cooperation between hardware resources and software, for example. Specifically, the image processing apparatus 10 includes a processor such as a central processing unit (CPU) (unillustrated). The processor reads and executes a program stored in a storage device (not illustrated), thereby realizing the functions of the deleted differential image generator 18, the added differential image generator 20, the region specifying unit 22, the image extracting unit 24, and the image classifying unit 26. The program is stored in the storage device via a storage medium such as a compact disc (CD) or a digital versatile disc (DVD), or via a communication path such as a network.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An image processing apparatus comprising:
at least one processor configured to implement:
a deleted differential image generator that generates, from first image data generated by reading an image of an unfilled or filled-in sheet and second image data generated by reading an image of a sheet being in a format identical to the unfilled or filled-in sheet and having a superimposed sheet superimposed thereon, deleted differential image data representing an image that is not represented in the second image data but is represented in the first image data; and
a region specifying unit that specifies a region where the superimposed sheet is represented in the second image data, based on a region where the deleted differential image data is.

2. The image processing apparatus according to claim 1,
wherein the unfilled sheet and the filled-in sheet include lines drawn thereon, and
wherein the region specifying unit specifies, based on a region where the lines represented in the deleted differential image data are, the region where the superimposed sheet is represented in the second image data.

3. The image processing apparatus according to claim 2,
wherein the unfilled sheet and the filled-in sheet include a plurality of first lines and a second line drawn thereon as the lines, the plurality of first lines extending in a first direction and being arranged at an interval along a second direction intersecting the first direction, the second line extending in the second direction and intersecting the plurality of first lines, and
wherein the region specifying unit specifies, with reference to ends of the plurality of first lines and the second line represented in the deleted differential image data, a boundary of the superimposed sheet represented in the second image data.

4. The image processing apparatus according to claim 3,
wherein, in a case where the plurality of first lines are represented, but the second line is not represented, in the deleted differential image data, the region specifying unit specifies positions separated from positions of the plurality of first lines represented in the deleted differential image data, by a length corresponding to the interval between every two of the plurality of first lines, as a boundary of the region where the superimposed sheet is represented in the second image data.

5. The image processing apparatus according to claim 1,
wherein the at least one processor is further configured to implement an extracting unit that extracts, from the second image data, image data in a region of the superimposed sheet specified by the region specifying unit.

6. The image processing apparatus according to claim 2,
wherein the at least one processor is further configured to implement an extracting unit that extracts, from the second image data, image data in a region of the superimposed sheet specified by the region specifying unit.

7. The image processing apparatus according to claim 3,
wherein the at least one processor is further configured to implement an extracting unit that extracts, from the second image data, image data in a region of the superimposed sheet specified by the region specifying unit.

8. The image processing apparatus according to claim 1,
wherein the at least one processor is further configured to implement:

an added differential image generator that generates, from the first image data and the second image data, added differential image data representing an image that is not represented in the first image data but is represented in the second image data; and an extracting unit that extracts, from the added differential image data, image data in a region of the superimposed sheet specified by the region specifying unit.

9. The image processing apparatus according to claim 2, wherein the at least one processor is further configured to implement:

an added differential image generator that generates, from the first image data and the second image data, added differential image data representing an image that is not represented in the first image data but is represented in the second image data; and an extracting unit that extracts, from the added differential image data, image data in a region of the superimposed sheet specified by the region specifying unit.

10. The image processing apparatus according to claim 3, wherein the at least one processor is further configured to implement:

an added differential image generator that generates, from the first image data and the second image data, added differential image data representing an image that is not represented in the first image data but is represented in the second image data; and an extracting unit that extracts, from the added differential image data, image data in a region of the superimposed sheet specified by the region specifying unit.

11. The image processing apparatus according to claim 5, wherein the at least one processor is further configured to implement an image classifying unit that specifies a type of the superimposed sheet represented in the extracted image data, and classifies the extracted image data based on the specified type.

12. The image processing apparatus according to claim 6, wherein the at least one processor is further configured to implement an image classifying unit that specifies a type of the superimposed sheet represented in the extracted image data, and classifies the extracted image data based on the specified type.

13. The image processing apparatus according to claim 7, wherein the at least one processor is further configured to implement an image classifying unit that specifies a type of the superimposed sheet represented in the extracted image data, and classifies the extracted image data based on the specified type.

14. The image processing apparatus according to claim 8, wherein the at least one processor is further configured to implement an image classifying unit that specifies a type of the superimposed sheet represented in the extracted image data, and classifies the extracted image data based on the specified type.

15. The image processing apparatus according to claim 9, wherein the at least one processor is further configured to implement an image classifying unit that specifies a type of the superimposed sheet represented in the extracted image data, and classifies the extracted image data based on the specified type.

16. The image processing apparatus according to claim 10, wherein the at least one processor is further configured to implement an image classifying unit that specifies a type of the superimposed sheet represented in the extracted image data, and classifies the extracted image data based on the specified type.

17. The image processing apparatus according to claim 1, wherein the superimposed sheet is one from among a test slip, a nursing record, a care note, and a prescription slip.

18. An image processing method comprising:

generating, from first image data generated by reading an image of an unfilled or filled-in sheet and second image data generated by reading an image of a sheet being in a format identical to the unfilled or filled-in sheet and having a superimposed sheet superimposed thereon, deleted differential image data representing an image that is not represented in the second image data but is represented in the first image data; and specifying a region where the superimposed sheet is represented in the second image data, based on a region where the deleted differential image data is.

19. A non-transitory computer readable medium storing a program causing a computer to execute a process for image processing, the process comprising:

generating, from first image data generated by reading an image of an unfilled or filled-in sheet and second image data generated by reading an image of a sheet being in a format identical to the unfilled or filled-in sheet and having a superimposed sheet superimposed thereon, deleted differential image data representing an image that is not represented in the second image data but is represented in the first image data; and specifying a region where the superimposed sheet is represented in the second image data, based on a region where the deleted differential image data is.

* * * * *